United States Patent [19]

Philippe et al.

[11] Patent Number: 5,096,713
[45] Date of Patent: Mar. 17, 1992

[54] RETINOIC ESTERS OF L-CLADINOSE, PROCESS FOR THEIR PREPARATION AND THEIR USE IN HUMAN OF VETERINARY MEDICINE AND IN COSMETIC COMPOSITIONS

[75] Inventors: Michel Philippe, Antony; Henri Sebag, Paris, both of France

[73] Assignee: L'Oreal, Paris, France

[21] Appl. No.: 493,114

[22] Filed: Mar. 15, 1990

[30] Foreign Application Priority Data

Mar. 16, 1989 [FR] France ............................ 89 03461

[51] Int. Cl.⁵ ...................... A61K 31/07; C07C 35/18
[52] U.S. Cl. ................... 424/427; 514/912; 568/824
[58] Field of Search ........................ 424/427; 514/912; 568/824

[56] References Cited

U.S. PATENT DOCUMENTS

| | | | |
|---|---|---|---|
| 3,984,544 | 10/1956 | Casmer et al. | 514/178 |
| 4,108,880 | 8/1978 | Gander et al. | 424/59 |
| 4,216,224 | 8/1980 | Yu et al. | 562/507 |

FOREIGN PATENT DOCUMENTS 0253393 7/1987 European Pat. Off. .
8418617 12/1984 France .
8900157 1/1989 PCT Int'l Appl. .

Primary Examiner—Thurman K. Page
Assistant Examiner—Carlos Azpuru
Attorney, Agent, or Firm—Cushman, Darby & Cushman

[57] ABSTRACT

Retinoic esters of L-cladinose have the formula

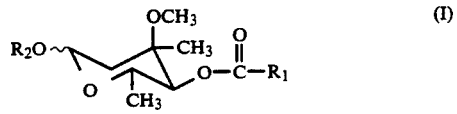

wherein the

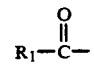

radical is (all trans) retinoyl, (13 cis) retinoyl or etretinoyl, and $R_2$ represents linear or branched alkyl having 1-24 carbon atoms; and the $\alpha$ and $\beta$ anomers and their mixtures.

These esters are usefully employed in human and veterinary medicines and in cosmetic compositions.

6 Claims, No Drawings

RETINOIC ESTERS OF L-CLADINOSE, PROCESS FOR THEIR PREPARATION AND THEIR USE IN HUMAN OF VETERINARY MEDICINE AND IN COSMETIC COMPOSITIONS

The present invention relates to new retinoic esters of L-cladinose, to a process for their preparation and to their use in human and veterinary medicine and in cosmetic compositions.

These new retinoic esters of L-cladinose are particularly useful in the topical and systemic treatment of dermatologic diseases linked to a keratinization disorder (differentiation-proliferation) and dermatologic diseases, or others, having inflammatory and/or immunoallergic components and in conjunctive tissue degeneration illnesses. These retinoic esters also exhibit anti-tumoral activity. Moreover, these esters can be employed in the treatment of atophy, be it cutaneous or respiratory and in the treatment of rheumatoid psoriasis.

The esters of the present invention can also be employed in treatments to combat skin aging.

They are also employed in the ophthalmologic field and principally in the treatment of corneopathies.

There have already been proposed, in French patent No. 84.18617 (2.556.348), new retinoids which are esters or amides of etretinic acid and a sugar, for the treatment of neoplasies, psoriasis and acne. These esters or amides have the formula

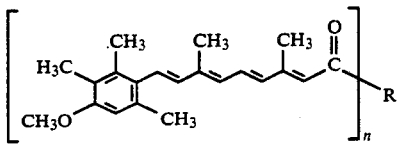

wherein

R represents the residue of a sugar linked by a bond of the ester type or the residue of an aminated sugar linked by an amide type bond, or derivatives of such sugars, and n is equal to 1 or 2.

In accordance with this patent, the sugar residue is derived preferably from glucose, maltose, trehalose or ribose or even a derivative of these sugars.

After significant studies it has now been noted, in a quite surprising and unexpected manner, that by using, as the sugar, L-cladinose, forming erythromycins A and B, for the formation of esters not only with etretinic acid but also with (all trans) and (13 cis) retinoic acids, it was possible to overcome the disadvantages of these acids, i.e. their toxicity and principally their teratogen characteristic.

The comparative studies carried out have, moreover, evidenced that these new properties were due essentially to the nature of the sugar employed for the esterification, namely, L-cladinose. In effect the esters corresponding to glucose, for example, do not provide the same detoxification and principally in that which concerns an all-trans chain.

The present invention relates to, as a new industrial product, retinoic esters of L-cladinose having the following general formula

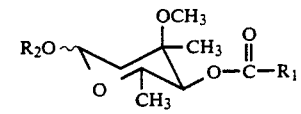

wherein

is either the (all trans) or (13 cis) retinoyl radical or the etretinoyl radical, and $R_2$ represents linear or branched alkyl having 1 to 24 carbon atoms, and the $\alpha$ and $\beta$ anomers and their mixture.

Representative linear or branched alkyl radicals having 1–24 carbon toms, include principally, methyl, ethyl, propyl, isopropyl, butyl, tert. butyl, octyl, nonyl, decyl, undecyl, dodecyl, tetradecyl, hexadecyl, octadecyl and 2-decyl tetradecyl radicals.

When the retinoic esters of L-cladinose are derived from etretinic acid they can be represented by a compound of the following general formula

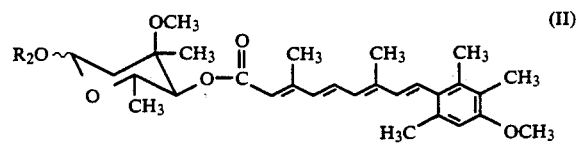

wherein $R_2$ has the same meaning given above in the definition of the compound of formula (I).

When the retinoic esters of L-cladinose are derived from (all trans) or (13 cis) retinoic acid, they can be represented by the following general formula

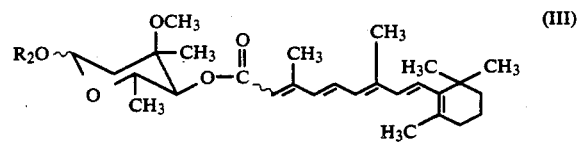

wherein $R_2$ has the same meaning as that given above in general formula (I).

Representative retinoic esters of L-cladinose in accordance with the present invention include, principally:

1. O-retinoyl (all trans)-4-O-methyl-1-$\alpha,\beta$-L-cladinose,
2. O-retinoyl (13 cis)-4-O-methyl-1-$\alpha,\beta$-L-cladinose,
3. O-etretinoyl (all trans)-4-O-methyl-1-$\alpha,\beta$-L-cladinose, and
4. O-retinoyl (all trans)-4-O-decyl-2'-tetradecyl-1-$\alpha,\beta$-L-cladinose.

The present invention also relates to a process for preparing the retinoic esters of L-cladinose such as defined above.

Various processes for the esterification of L-cladinose in the 4-position can be employed, but, preferably the esterification is carried out in an anhydrous organic solvent medium such as tetrahydrofuran, alone or in admixture with another organic solvent such as pyridine or N,N-dimethylformamide, by reacting an excess of the mixed anhydride, of either etretinic acid or (all trans) retinoic or (13 cis) retinoic acid, prepared in situ, for example, from ethyl chloroformate and the selected acid, on a monoether, in position 1, of L-cladinose.

Other esterification procedures can be employed, and principally the method using the imidazolides of the selected acids in an anhydrous solvent, such as pyridine or N,N-dimethyl formamide in the presence of a base such as potassium tert. butanolate or sodium imidazolide. However, these methods generally give lower yields.

The monoethers in position 1 of L-cladinose are obtained by conventional etherification methods by reacting L-cladinose with the selected alcohol ($R_2OH$), in the presence of a mineral acid such as sulfuric or hydrochloric acid or an organic acid such as paratoluene sulfonic acid, optionally in an organic solvent such as N,N-dimethylformamide at a temperature of about 80° C.

The compounds in accordance with the present invention are quite particularly useful in the following fields:

(1) for the treatment of dermatologic diseases linked to a keratinization disorder based on differentiation and proliferation and principally for the treatment of acne vulgaris, comedons, polymorphs, kystic nodule acne, conglobata, senile acne, and secondary acne such as solar, medicinal and professional acne;

(2) for the treatment of other types of keratinization disorders and principally ichthyoses, ichthyosiform states, Darier malady, palmoplantaire keratodermies, leucoplasies and leucoplasiform states, lichen;

(3) for the treatment of other dermatologic diseases linked to a keratinization disorder having an inflammatory and/or immunoallergic component and, principally, all forms of psoriasis be it cutaneous, mucous or ungual, and even psoriasic rheumatism or even cutaneous atophy, such as eczema or respiratory atophy. These compounds can also be employed in certain inflammatory diseases not exhibiting a keratinization disorder;

(4) for the treatment of all dermic or epidermic proliferations be they benign or malignant, be they of viral origin such as common warts, plane warts, and verruciform epidermodysplasie. The proliferations can also be those which are induced by ultraviolet radiation, principally in the framework of baso epithelioma and cellular spino;

(5) for the treatment of other dermatologic diseases such as blistery dermatoses and collagen maladies;

(6) for the treatment of certain ophthalmologic disorders, principally corneopathies;

(7) to combat against skin aging, be it photo-induced or not; and (8) to prevent or heal the scars of epidermic and/or dermic atophy induced by local or systemic corticosteroids, or any other form of cutaneous atophy.

The present invention also relates to the use of the retinoic esters of L-cladinose, such as defined above, as an active agent for compositions having a therapeutic use.

The therapeutic compositions, intended principally for the treatment of the above mentioned diseases contain, in a pharmaceutically acceptable support or vehicle, at least one retinoic ester of L-cladinose, such as defined above by general formula (I).

These retinoic esters of L-cladinose are generally administered at a daily dosage of about 0.01 mg/kg to 50 mg/kg of body weight.

As the support for the compositions there can be used any conventional support, the active compound being found either in the dissolved state or in the dispersed state in the support or vehicle.

The administration can be effected enterally, parenterally, topically or ocularly. When administered enterally, the therapeutic compositions can be provided in the form of tablets, gelules, lozenges, syrups, suspensions, solutions, powders, granules, or emulsions. When administered parenterally, the composition can be provided in the form of solution or suspensions for perfusion or injection.

When administered topically, the therapeutic compositions, based on the retinoic esters of L-cladinose in accordance with the invention, can be provided in the form of ointments, tinctures, creams, pomades, powders, patches, impregnated pads, solutions, lotions, gels, sprays or even suspensions.

When administered ocularly, the compositions are principally eye washes.

These therapeutic compositions contain at least one retinoic ester of L-cladinose, such as defined above, in an amount ranging, preferably, from 0.001 to 5 percent by weight relative to the total weight of the composition.

The retinoic esters of L-cladinose of general formula (I) are also usefully employed in the cosmetic field and in particular for body and hair hygiene and principally for the treatment of skin having acne tendencies, for hair growth, to combat falling hair, to combat against an oily appearance of the skin or hair, for protection against the harmful effects of the sun and for treatment of physiologically dry skin.

The present invention then also relates to cosmetic compositions containing in a cosmetically acceptable vehicle or support at least one retinoic ester of L-cladinose of general formula (I), this composition being provided principally in the form of a lotion, a gel, a soap, a shampoo, a stick, a spray or an aerosol foam.

The concentration of the retinoic ester of L-cladinose of formula (I) in the cosmetic compositions is generally between 0.0001 and 5 percent by weight and preferably between 0.001 and 3 percent by weight based on the total weight of said cosmetic composition.

The therapeutic and cosmetic compositions, in accordance with the present invention, can also contain inert or even pharmacodynamically or cosmetically active additives and principally: hydrating agents such as thiamorpholinone and its derivatives or urea; anti-seborrheic or anti-acne agents such as S-carboxymethylcysteine, S-benzyl cysteamine and their salts and their derivatives, thioxolone or benzoyl peroxide; antibiotics such as erythromycin and its esters, neomycin, tetracyclines or 4,5-polymethylene-3-isothiazolinones; agents promoting hair growth such as "Minoxidil" (2,4-diamino-6-piperidino-pyrimidine-3-oxide) and its derivatives, Diazoxide (7-chloro-3-methyl1,2,4-benzothiadiazine-1,1-dioxide) and Phenytoin (5,5-diphenylimidazolidine-2,4-dione); steroidal and non-steroidal anti-inflammatory agents; carotenoids and principally β-carotene; anti-psoriasic agents, such as anthralin and its derivatives and 5,8,11,14-eicosatetraynoic and 5,8,11-triynoic acids and their esters and their amides.

The compositions in accordance with the present invention, be they for therapeutic or cosmetic use, can also contain flavor improving agents, preservatives, stabilizers, humidity regulators, pH regulators, osmotic pressure modifiers, emulsifiers, UV-A and UV-B filters, antioxidants such as α-tocopherol, butylhydroxyanisole or butylhydroxytoluene.

As an illustration and without any limiting character, the following are several examples of the preparation of the active compounds of formula (I), as well as several examples of compositions containing them, all in accordance with the present invention.

EXAMPLES OF PREPARATION

EXAMPLE 1

Preparation of O-retinoyl (all trans)-4-O-methyl-1-α,β-L-cladinose

In a round bottom flask, under an inert atmosphere, 5 g (16.6 mmoles) of retinoic acid (all trans) are dissolved in 35 ml of anhydrous tetrahydrofuran; the reaction mixture is cooled to 0° C. and then poured into 3 ml (38 mmoles) of anhydrous pyridine and 1.6 ml (16.6 mmoles) of ethyl chloroformate. The solution is stirred for 5 minutes and 2.5 g (30 mmoles) of sodium bicarbonate are added. Thereafter, 1.3 g (6.8 mmoles) of O-methyl-1-α,β-L-cladinose, previously dissolved in 150 ml of tetrahydrofuran, are added. The reaction mixture is then stirred for 10 hours while permitting the temperature thereof to return to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is then chromatographed on a silica gel column (H.P.L.C.) using as the eluant: ethyl acetate (3)/hexane (7) thereby resulting in the isolation of 1.9 g (59% yield) of O-retinoyl (all trans)-4-O-methyl-1-α,β-L-cladinose.

Microanalysis: $C_{29}H_{44}O_5.1H_2O$; $M=480.7$

|  | C | H |
|---|---|---|
| Calculated, % | 70.98 | 9.44 |
| Found, % | 70.40 | 9.34 |

The NMR of $^{13}C$ (CDCl$_3$, ref. internal T.M.S.)

Confirmation of the all trans configuration of the retinoic chain is given by the chemical displacement of the C'$_{14}$ at 117.53 ppm. The negative γ effects at 5 (−2.6 ppm for the α-anomer and −2.1 ppm for the β-anomer) indicate the position of the ester at 4.

EXAMPLE 2

Preparation of O-retinoyl (13 cis)-4-O-methyl-1-α,β-L-cladinose

In a round bottom flask, under an inert atmosphere, 10 g (33.2 mmoles) of retinoic acid (13 cis) are dissolved in 90 ml of anhydrous tetrahydrofuran; the reaction mixture is cooled to 0° C. and then poured into 7 ml of anhydrous pyridine and 3.2 ml (33.2 mmoles) of ethyl chloroformate. The solution is stirred for 5 minutes and 5 g of sodium bicarbonate are added. Thereafter, 2.5 g (13.1 mmoles) of O-methyl-1-α,β-L-cladinose, previously dissolved in 200 ml of tetrahydrofuran, are added. The reaction mixture is then stirred for 10 hours while permitting the temperature thereof to rise to ambient temperature (chromatography on thin layer silica gel: methylene chloride/10% methanol). The solution is poured into 60 ml of water and then extracted with ethyl acetate. The organic phase is dried on magnesium sulfate, filtered and then concentrated under a partial vacuum. The resulting crude product is then chromatographed on a silica gel column (H.P.L.C.) using as the eluant: ethyl acetate (3)/hexane (7) thereby resulting in the isolation of 4 g (64% yield) of O-retinoyl (13 cis)-4-O-methyl-1-α,β-L-cladinose.

Microanalysis: $C_{29}H_{44}O_5.1.5H_2O$; $M=499.7$

|  | C | H |
|---|---|---|
| Calculated, % | 69.70 | 9.46 |
| Found, % | 69.58 | 9.34 |

The NMR of $^{13}C$ (CDCl$_3$, ref. internal T.M.S.)

Negative γ effects at 5 (−2.6 ppm) and at 3 (−2.1 ppm) respectively for the o and B anomers, show that the ester is in position 4. The 13 cis configuration of the retinoic chain is given by the chemical displacement of the C'$_{14}$ at 115.5 ppm.

EXAMPLE 3

Preparation of O-etretinoyl (all trans)-4-O-methyl-1-α,β-L-cladinose

In a round bottom flask, under an inert atmosphere, 716 mg (6.6 mmoles) of ethyl chloroformate and 20 ml of tetrahydrofuran are introduced. The solution is stirred and cooled to −5° C.

Slowly, without exceeding 0° C., a solution containing 2.2 g (6.4 mmoles) of etretinoic acid, 660 mg (6.6 mmoles) of triethylamine and 20 ml of tetrahydrofuran is added. The reaction mixture is then stirred for 1 hour and 30 minutes at ambient temperature. The salts of triethylamine are removed by filtration.

The filtrates are then introduced at ambient temperature and under an inert atmosphere into a round bottom flask containing 370 mg (2.1 mmoles) of O-methyl-1-α,β-L-cladinose and 0.6 ml of anhydrous pyridine (6.6 mmoles).

The reaction mixture is then stirred for 15 hours.

The reaction is followed by chromatography on a thin layer of silica gel using as the eluant: ethyl acetate (6)/heptane (4).

The reaction mixture is concentrated, then taken up in toluene and purified by chromatography on a silica gel column (H.P.L.C.) using as the eluant: ethyl acetate (6)/heptane(4) thereby resulting in the isolation of 180 mg (17.6% yield) of O-etretinoyl (all trans)-4-O-methyl-1-α,β-L-cladinose.

|  | C | H |
|---|---|---|
| Calculated, % | 72.26 | 8.49 |
| Found, % | 72.36 | 8.55 |

NMR of $^{13}C$ (CDCL$_3$, ref. internal. T.M.S.)
The spectrum is in agreement with the proposed structure.

| A-Gels for the topical treatment of acne | |
|---|---|
| 1. Hydroxypropyl cellulose | 1 g |
| Butylhydroxytoluene | 0.05 g |
| O-retinoyl (13 cis)-4-O-methyl-1-α,β-L-cladinose | 0.1 g |
| Isopropanol, sufficient amount for | 100 g |
| 2. Hydroxypropyl cellulose | 1.5 g |

-continued

| | |
|---|---|
| Butylhydroxytoluene | 0.05 g |
| O-retinoyl (all trans)-4-O-methyl-1-α,β-L-cladinose | 0.075 g |
| Isopropanol, sufficient amount for | 100 g |
| B-Lotion for the topical treatment of acne | |
| Butylhydroxytoluene | 0.05 g |
| O-retinoyl (13 cis)-4-O-methyl-1-α,β-L-cladinose | 0.7 g |
| Triglycerides of $C_8$–$C_{12}$ fatty acids, sufficient amount for | 100 g |
| C-Stick for the treatment of acne | |
| White petrolatum | 52.7 g |
| Petrolatum oil | 15 g |
| Raffinated paraffin | 32 g |
| O-retinoyl (all trans)-4-O-methyl-1-α,β-L-cladinose | 0.3 g |

We claim:

1. A retinoic ester of L-cladinose having the formula (I)

wherein the $$R_1-\overset{O}{\underset{\|}{C}}-$$

radical is (all trans) retinoyl, (13 cis) retinoyl or etretinoyl, and $R_2$ represents linear or branched alkyl having 1–24 carbon atoms, and the α and β anomers and their mixtures.

2. The retinoic ester of claim 1 wherein said linear or branched alkyl is methyl, ethyl, propyl, isopropyl, butyl, tert. butyl, octyl, nonyl, decyl, undecyl, dodecyl, tetradecyl, hexadecyl, octadecyl or 2-decyl tetradecyl.

3. The retinoic ester of claim 1 derived from etretinoic acid and having the formula (II)

wherein $R_2$ has the meaning given in claim 1.

4. The retinoic ester of claim 1, derived from (all trans) or (13 cis) retinoic acid and having the formula (III)

wherein $R_2$ has the meaning given in claim 1.

5. The retinoic ester of claim 1 selected from the group consisting of
O-retinoyl (all trans)-4-O -methyl-1-α,β-L-cladinose,
O-retinoyl (13 cis)-4-O -methyl-1-α,β-L-cladinose,
O-etretinoyl (all trans)-4-O-methyl-1-α,β-L-cladinose, and
O-retinoyl (all trans)-4-O-decyl-2'-tetradecyl-1-α,β-L-cladinose.

6. A process for the preparation of the retinoic ester of claim 1 comprising reacting an excess of a mixed anhydride of etretinic acid or of (all trans) or (13 cis) retinoic acid, prepared in situ, with a monoether, in position 1, of L-cladinose, in an organic solvent medium selected from tetrahydrofuran, alone, or in admixture with pyridine of N,N-dimethylformamide.

* * * * *